United States Patent [19]

Ackland et al.

[11] Patent Number: 4,653,337

[45] Date of Patent: Mar. 31, 1987

[54] CONTAINERS FOR USE IN DETECTING MICRO-ORGANISMS

[75] Inventors: Martin R. Ackland; Roderick M. De'ath, both of Wantage, England

[73] Assignee: Metal Box p.l.c., Reading, England

[21] Appl. No.: 825,616

[22] Filed: Feb. 3, 1986

[30] Foreign Application Priority Data

Mar. 8, 1985 [GB] United Kingdom ............... 8506097

[51] Int. Cl.[4] .......................................... G01N 27/02
[52] U.S. Cl. .................................... 73/866.5; 324/447
[58] Field of Search ............... 422/61, 202, 68; 204/400, 403; 435/287, 296; 73/864.81, 864.83, 864.84, 864.85, 864.86, 864.87, 864.91, 866.5; 324/446, 447, 450, 439

[56] References Cited

U.S. PATENT DOCUMENTS

| | | | |
|---|---|---|---|
| 2,830,260 | 4/1958 | Chiocca | 324/446 |
| 3,715,189 | 2/1973 | Nighohossian et al. | 422/61 |
| 3,743,581 | 7/1973 | Cady et al. | 324/439 |
| 3,871,961 | 3/1975 | Gianessi | 435/287 |
| 3,875,012 | 4/1975 | Dorn et al. | 435/296 |
| 3,939,035 | 2/1976 | Fletcher et al. | 204/400 |
| 4,264,728 | 4/1981 | Wilkens | 204/403 |
| 4,407,958 | 10/1983 | DeGraff, Jr. | 435/287 |
| 4,416,984 | 11/1983 | Wheeler, Jr. | 435/287 |

Primary Examiner—Michael J. Tokar
Assistant Examiner—Robert R. Raevis
Attorney, Agent, or Firm—Diller, Ramik & Wight

[57] ABSTRACT

For use in detecting micro-organisms in a sample of a substance, a container for holding the sample consists of a glass bottle and closure in the form of an elastomeric bung, the bung being provided with a pair of chambers each housing a respective electrode until the container is required for use, when the electrodes are urged upwardly, breaking through a membrane of the bung to bring the electrodes into contact with the test sample in the bottle.

14 Claims, 7 Drawing Figures

CONTAINERS FOR USE IN DETECTING MICRO-ORGANISMS

BACKGROUND OF THE INVENTION

1. Field of the Invention

The present invention relates to containers for use in detecting micro-organisms in samples of substances, which may consist either of substances intended for human consumption, such as foods, drinks or pharmaceuticals, or of pathological or other laboratory substances.

2. Description of the Prior Art

A number of known methods for detecting micro-organisms include the use of electrical cells, in which electrodes are in contact with a micro-biological sample in a growth medium. Such methods include measurement of sample impedance, measurement of dissolved oxygen concentration by applying a pulsed voltage to the growth medium/electrolyte and, in a third method, changes in potential differences between two electrodes immersed in a growth medium containing the micro-organisms are monitored. This latter method has several advantages over other methods of detecting micro-organisms and apparatus for carrying out this method is described and claimed in our copending British patent application No. 8317685 (publication No. 2142433) and International application No. PCT/GB84/00235 (publication No. WO85/00225)). Nevertheless, the present invention is applicable to any method of micro-organism detection requiring the use of a cell (or test container) in which one or more electrodes would have to be in contact with the growth medium.

A problem has arisen, particularly in the case of disposable test containers manufactured with growth medium in situ and which are expected to have a shelf life of up to, say, 18 months, before a microbological sample is introduced to the container for testing. During storage, the electrodes are in contact with the growth medium and hence are susceptible to corrosion. Corrosion of the electrode(s) gives raised concentrations of cations in the growth medium, which might inhibit growth of the micro-organisms to be tested, and hence lead to spurious test results.

An attempt has been made to mitigate the likelihood of electrode corrosion by providing test containers with electrode(s) in the lid, so that the container can be stored with the electrode(s) out of contact with the growth medium until the test is due to start, when the container is inverted to bring the sample into contact with the electrode(s). Nevertheless, it has been found that the electrode(s) may still show signs of corrosion because of being kept in contact with the vapour above the growth medium. The method referred to above, involving changes in potential difference between two passive electrodes, benefits from using electrodes of dissimilar metals, one being say aluminium or zinc and the other being a noble metal, such as gold or platinum, because there is a greater drop in potential difference once growth of the micro-organism has reached a particular concentration. The greater the change in potential difference, the less significant is the electrical noise in the system, so that the drop will be more readily apparent. As a result of the need for dissimilar metals, at least one of the electrodes is likely to be relatively prone to corrosion.

SUMMARY OF THE INVENTION

According to a first aspect of the invention there is provided a container for use in detecting micro-organisms in a sample of a substance, comprising a container body having an opening therein, a closure located in said opening, and at least two electrodes, which are contactable with a sample in the container, wherein the closure comprises a chamber in which at least a portion of at least one of the electrodes is housed, the closure further comprising frangible wall means which separate the chamber from the interior of the container body, whereby the said electrode portion is isolated from the contents of the container and stored aseptically in the chamber, whereas, when the container is required for use, the wall means can be ruptured to bring the electrode portion into contact with the contents of the container.

Suitably, the closure comprises an elastomeric bung, and the wall means comprises a membrane integral therewith. In this embodiment, the container may further comprise a retaining means for retaining the bung in the opening in the container body, and preferably orientation means are provided between the bung and the retaining means, whereby the retaining means is assured of being at a predetermined orientation relative to the said electrode.

In an alternative embodiment, the closure comprises a cup-shaped stopper, open inwardly towards the interior of the container body, and the wall means comprises a diaphragm releasably retained adjacent the rim of the cup-shaped stopper.

Either at least a portion of both of said two electrodes are housed in the chamber or in respective chambers in the closure, or at least a part of the container body constitutes the other of said two electrodes.

Either the container body comprises a further, resealable opening adapted to enable aseptic introduction of the sample of a substance to the interior of the container, or the closure comprises a portion adapted to enable aseptic introduction of the sample to the interior of the container.

The interior of the container body may be under reduced pressure, when the wall means must be capable of withstanding rupture under a pressure difference of 1 atmosphere.

The container may further comprise an annular member threadedly engaged with the container body and cooperable with the electrode, whereby, on relative rotation between the annular member and container body, the electrode is displaced to cause rupture of the wall means.

According to a further aspect of the invention, there is provided apparatus for use in detecting micro-organisms, comprising one or more such containers, and a container-mounting member with means for receiving and locating the or each container, wherein the receiving and locating means comprises means for cooperating with the or each electrode housed in the closure, whereby, when the container is received by the container-mounting member, the or each electrode is displaced to cause rupture of the wall means.

Suitably, the container comprises connecting means cooperable with said receiving and locating means, for releasable connection between the container and the container-mounting member.

Preferably, orientation means are provided between the connecting means and the receiving and locating means, and between the connecting means and the electrode, whereby, when the container is connected to the container-mounting member, the electrode is at a predetermined orientation relative thereto.

DETAILED DESCRIPTION OF THE PREFERRED EMBODIMENTS

Figure 1:
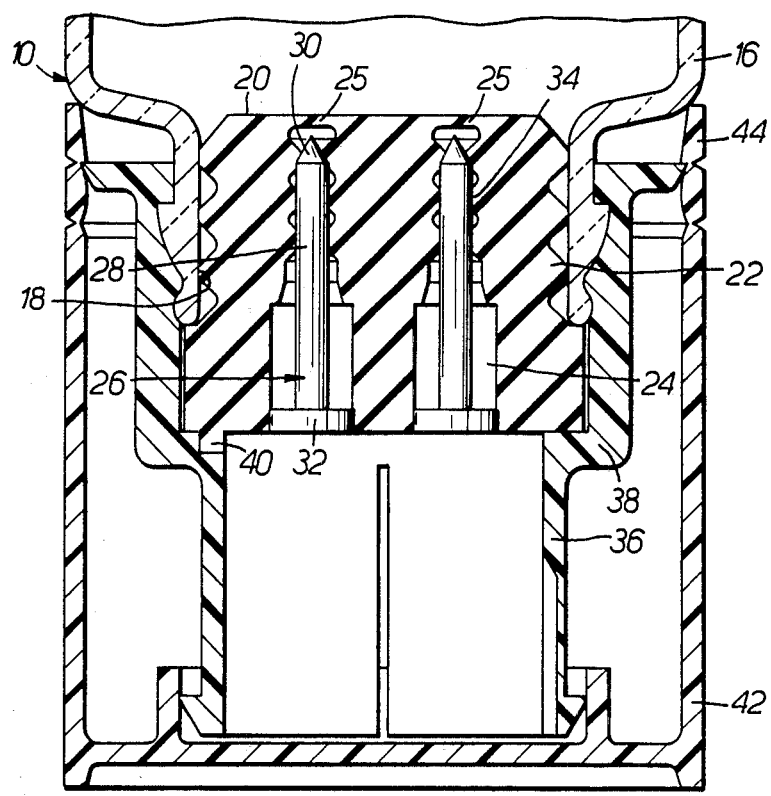
FIG. 1 is a longitudinal section through the lower part of a container in accordance with the present invention.
Figure 2:
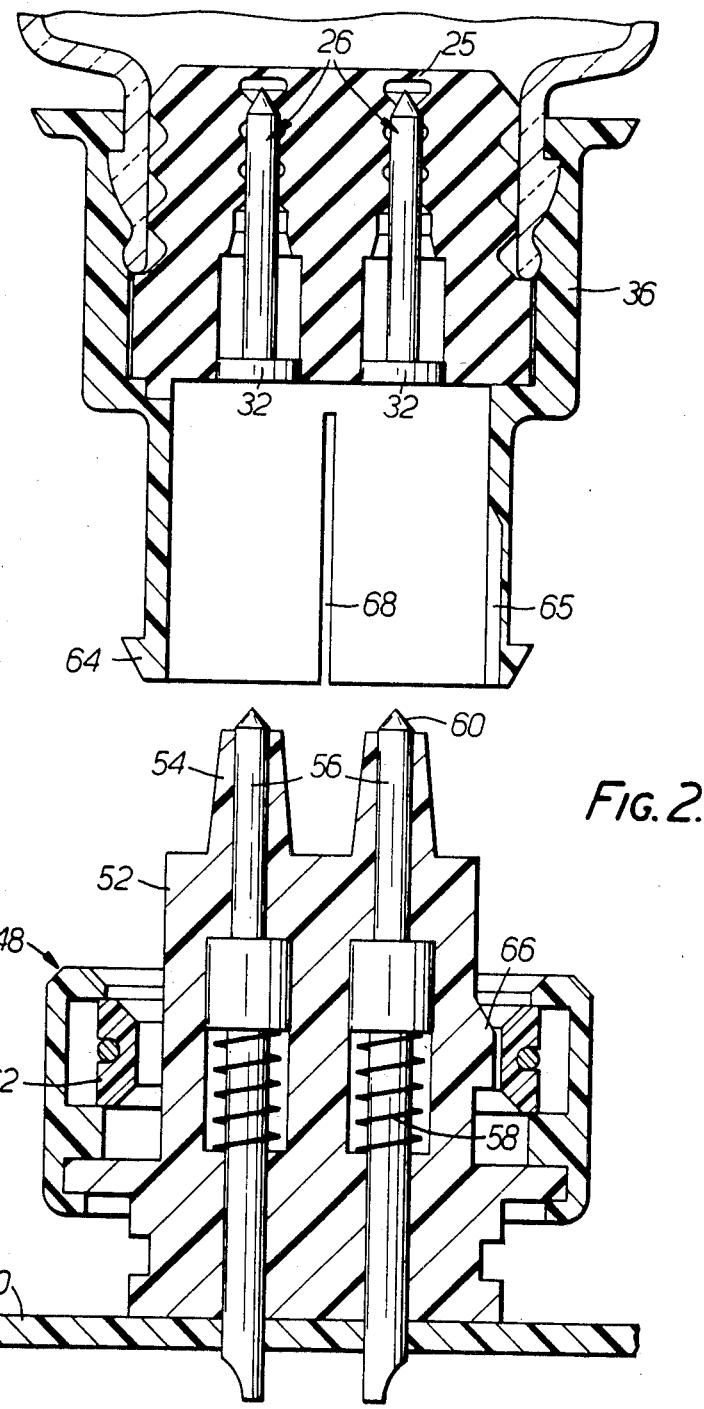
FIG. 2 is a longitudinal cross-section through the lower part of the container of FIG. 1 held above and ready for connection with a socket, shown in longitudinal section, of a container-mounting member.
Figure 3:
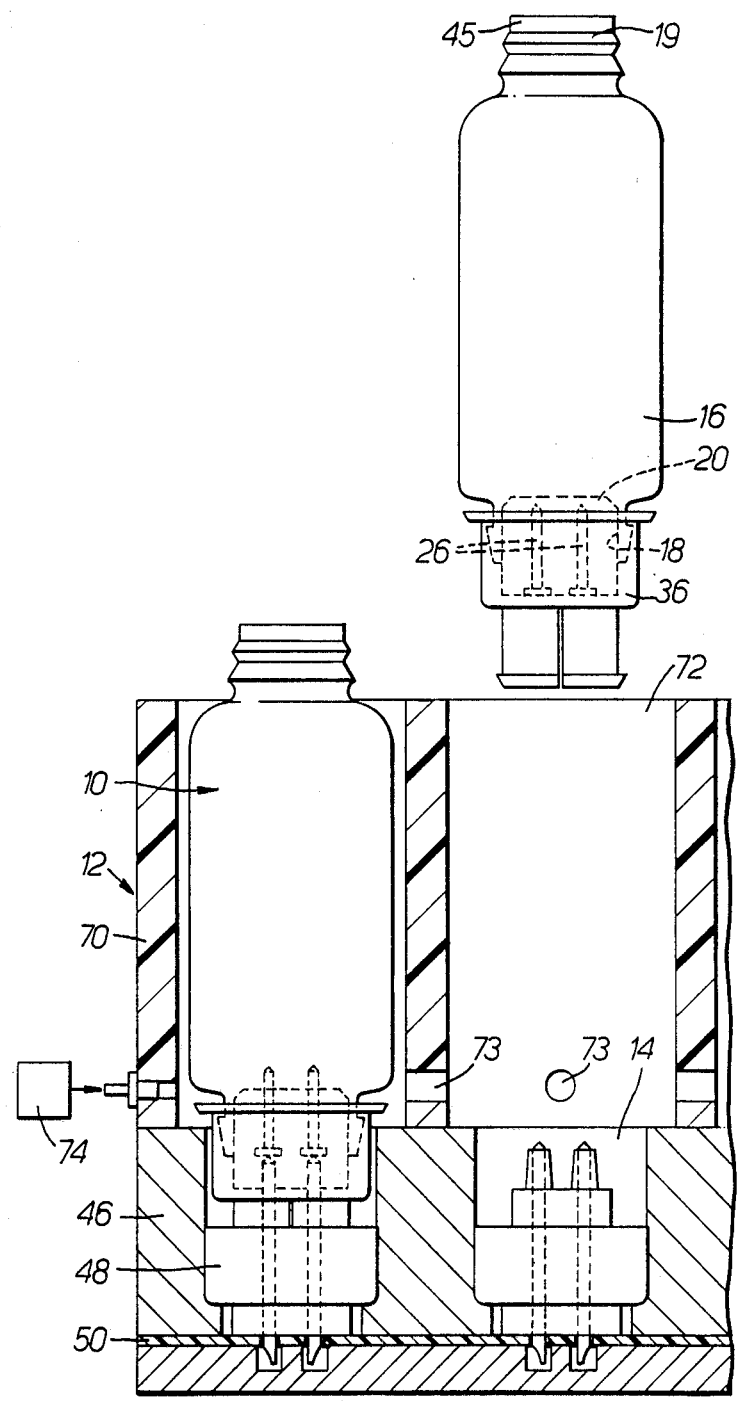
FIG. 3 is a schemmatic longitudinal section through the container-mounting member, showing one container located in its respective socket and a second container held above, ready for insertion into its respective socket.

Referring to FIGS. 1 to 3 of the drawings, there is shown a first embodiment of a container according to the invention, for use in detecting micro-organisms. The container 10 is one of a plurality of containers adapted to be received and located in a container-mounting member 12 (FIG. 3) comprising a plurality of cylindrical recesses 14 (say a total of 64) each of which is adapted to receive and locate an individual container 10. The container-mounting member 12 will be discussed in greater detail below.

The container 10 comprises a container body, in the form of a double ended glass bottle 16 (FIG. 3) having openings 18, 19 at opposite ends of the bottle 16, the openings being defined by neck portions of the bottle. Received in the lower opening 18 of the bottle is a substantially cylindrical elastomeric bung 20 and, to ensure that air-tight fit of the bung in the opening 18, the outer cylindrical surface of the bung 20 is provided with a plurality of integral annular ribs 22 spaced apart from one another.

The bung 20 constitutes a closure for the opening 18 of the bottle 16 and comprises a pair of axially extending chambers 24, spaced either side of the axis of the bung. The chambers are elongate, generally cylindrical but taper towards a closed end constituted by a frangible membrane 25 integrally formed with the elastomeric bung 20.

Each chamber 24 houses a respective electrode 26, each of which comprises a stem 28 having a pointed tip 30 at one of its ends and, at the opposite end, a metal button 32 in good electrical contact with the stem of the electrode 26. The stem 28 of each electrode is in close, air-tight contact with a series of spaced annular ribs 34 provided on the walls of each chamber and the button 32 is also in contact with the wall of the respective chamber 24. These measures ensure that the electrodes 26 are encapsulated in their respective chambers 24 in an aseptic state until testing of the sample is due to start.

To ensure that the bung 20 is retained in the opening 18 of the bottle 16, there is provided a connector 36 of a stepped cylindrical configuration. During testing of a sample, the contents of the bottle 16 may be subject to increased pressures, for instance during autoclaving or as a result of gas produced during growth of the micro-organism and it is for this reason that the connector 36 is required to retain the bung 20 in the bottle 16. The connector 36 is permanently secured to the neck of the bottle, for instance by a crown fitting and the bung 20 is retained in the bottle by abutting a step 38 of the connector 36. The connector is preferably made of a rigid material, preferably a plastics such as polypropylene. For reasons which will be described hereinbelow, orientation means 40, in the form of a lug on the bung 20 mating with a recess in the connector 36 are provided, so that the connector has a predetermined orientation with respect to the electrodes 26 housed in the bung 20.

The container is provided with an overcap 42, which acts to protect the bung and electrodes from ingress of contamination. The overcap also acts as a stand for the container 10 when it is not inserted in the container-mounting member 12. The overcap 42 can be releasably secured to the connector 36 by a removable tamper-proof ring 44.

The container is used in the following way. With its overcap 42 still in place (FIG. 1), the container has a sample of the substance to be tested introduced aseptically, by means of a hypodermic needle, through a rubber stopper 45 (FIG. 3) disposed in the opening 19 of the bottle 16. The stopper 45 itself may have been protected, during storage of the container, by its own removable overcap (not shown).

The overcap 42 is now removed (FIG. 2) and the container is then ready for insertion into the container-mounting member 12, (FIGS. 2 and 3) which generally comprises a block 46 provided with a plurality of spaced, fixed sockets 48, electrically interconnected via a printed circuit board 50. One of these fixed sockets 48 is shown in detail in FIG. 2 and generally comprises a cylindrical body 52 of rigid material integrally formed with two upwardly projecting probes 54. Housed within this cylindrical body 52 is a pair of spaced electrical contacts 56 biased upwardly by a respective spring 58 and each having a pointed tip 60. Surrounding the cylindrical body 52 and spaced therefrom is a tension ring 62 adapted to engage a collar 64 provided at the lower edge of the connector 36. Orientation means are provided between the connector 36 and fixed socket 48 in the form of a longitudinally extending keyway 65 on the connector 36 cooperable with an axially extending lug 66 on the cylindrical body 52 of the fixed socket 48.

To insert the container 10 into the container-mounting member 12, the connector 36 is located around the upper part of the cylindrical member 52 and, once the orientation means 65, 66 have been engaged, the container 10 is urged downwardly to push the collar 64 of the connector 36 past the tension ring 62 of the fixed socket 48. Although the connector 36 is of relatively rigid material, a certain resilience is provided by two opposing slots 68 in the connector, to allow the collar 64 to spring back once it is past the tension ring 62. The connector 36 serves to connect releasably the container 10 in the container-mounting member 12 and ensures correct orientation between the electrical contacts 56 of the socket and electrodes 26 of the container by virtue of the orientation means 40, between bung 20 and connector 36, and the orientation means 65, 66 between connector 36 and fixed socket 48.

As the container 10 is pushed downwardly into a respective recess 14 in the container-mounting member12, the probes 54 engage the buttons 32 on the electrodes 26, urging the electrodes to be displaced upwardly and thus causing the pointed ends 30 of the electrodes to pierce the respective membrane 25 separating each chamber 24 from the interior of the bottle 16. The electrodes 26 are now available for contact with the contents of the bottle 16, as shown in the left-hand container 10 of FIG. 3.

The container-mounting member 12 comprises a further block 70 located over, and releasably connected to, the block 46, and provided with a plurality of apertures 72 which communicate with respective recesses 14 in the block 46. With the apertures 72 aligned with their respective recesses 14, the blocks 46 and 70 are releasably fastened together. The block 70 acts as a jacket to provide a controlled temperature environment for bottles 16 which are located in the container mounting member 12, and, for this reason, the block 70 comprises conduits 73 for supplying heated air by fan assistance from a supply 74. The temperature-controlled environment for the bottles 16 ensures that growth of the micro-organism can be carried out at temperatures controlled to $\pm \frac{1}{2}C°$.

The electrical contacts 56 of the sockets 48 in the container-mounting member 12 are pointed and biased upwardly so as to ensure good electrical contact with the buttons 32 of the electrodes 26, the pointed tips breaking through any oxide formation on the surface of the buttons 32, the outer surfaces of which are not protected from the air during storage of the container 10.

Figure 4:
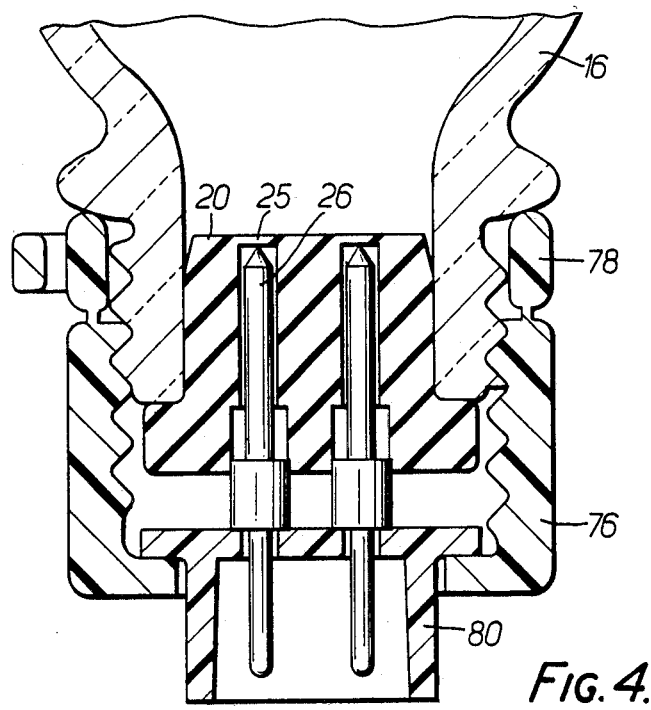
FIG. 4 illustrates a longitudinal section through the lower part of an alternative embodiment of container in accordance with the invention.
Figure 5:
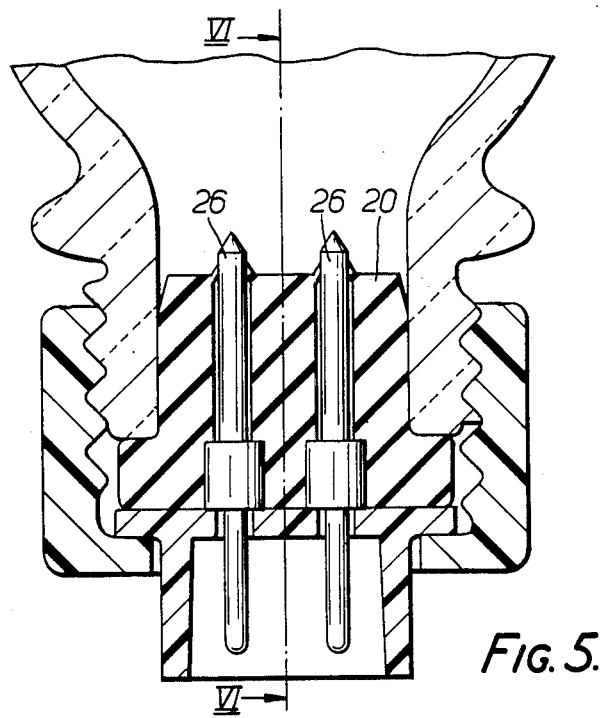
FIG. 5 is a longitudinal section through the container of FIG. 4, the container being ready for use in testing a micro-biological sample.
Figure 6:
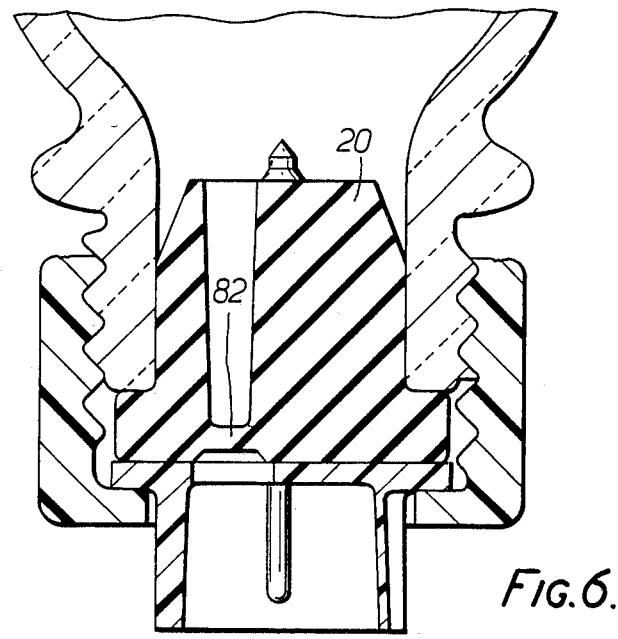
FIG. 6 shows the container in section taken along the line VI—VI of FIG. 5.

Referring to FIGS. 4 to 6 of the drawings, there is shown an alternative embodiment of container, again comprising electrodes housed in respective chambers 24 of an elastomeric bung 20, until required for use when they are urged towards the interior of the bottle 16. In this embodiment, however it is not the fixed socket 48 of the container-mounting member 12 which urges the electrodes into contact with the contents of the container, as in the previous embodiment, but instead the container 10 is provided with an annular member 76 threadedly engaged on the neck of the bottle 16. A tamper-proof ring 78 is removed and the annular member 76 screwed onto the bottle 16, drawing a connector 80 upwardly, which connector urges the electrodes 26 to pierce the membranes 25, thus bringing the electrodes 26 into contact with the sample in the container (FIG. 5).

In FIG. 6, it can be seen that the bung 20 is provided with a region 82 of reduced thickness and it is through this region 82 that the sample may be injected into the bottle 16. In this embodiment, the bottle can be a normal bottle having a single neck defining a single opening, rather than the bottle of FIG. 3 having openings at opposite ends.

Figure 7:
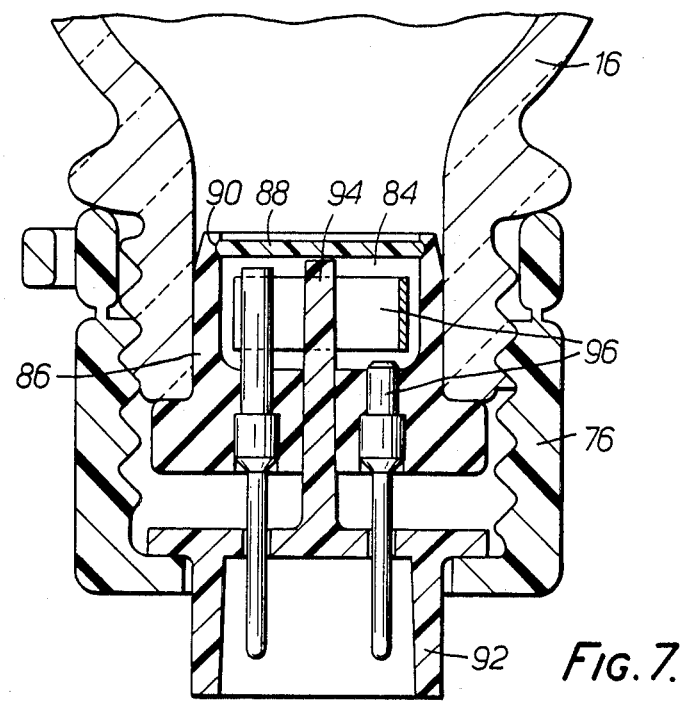
FIG. 7 illustrates a further alternative embodiment of container according to the invention.

In FIG. 7, there is shown a further alternative embodiment, which is similar to that of FIGS. 4 to 6 in having an annular member 76 threadedly engaged with the neck of the bottle 16, but the electrodes are housed in a single chamber 84 in a cup-shaped stopper 86. The chamber 84 is separated from the interior of the bottle 16 before use of the container by a diaphragm 88, which is push-fitted into a recess 90 adjacent the rim of the cup-shaped stopper 86. In this embodiment, the connector 92 comprises an upwardly directed, centrally disposed spigot 94 so that, on rotation of the annular member 76, the spigot pushes against the diaphragm 88 to release it from the recess 90, thus exposing the electrodes to the contents of the bottle 16. One of the electrodes 96 comprises a curved plate to extend its contact area with the sample.

In each of the embodiments, one of the electrodes is a noble metal such as gold or platinum and the other electrode is a dissimilar metal, such as aluminium or zinc.

The material of the glass bottle 16 may be a neutral sodaglass or a boro-silicate glass.

In all the embodiments, the electrodes 26 or 96 are retained in an aseptic chamber within the closure for the container until required for use and it is possible to use a number of known methods during assembly of the closure and container to ensure that the chamber 24 or 84 is sterile. Such methods include radiation, heat (by autoclave) or chemical cleaning, for instance by ethylene oxide so as to sterilize the electrode in the container closure.

Preferably the various components of the container-mounting member 12 are separable for cleaning, in the event that the member 12 should become contaminated by accidental spillage of a sample. The containers themselves are disposable, so that there is no risk of contamination from previous samples or of infecting personnel who have to clean the container for re-use.

Various modifications are possible, such as in the means for introduction of the sample. For instance, instead of a bung additional to the electrode(s)-containing closure, or a weakened area of the closure, the material of the container body could itself comprise a resealable plastics material through which the sample can be injected aseptically.

We claim:

1. A container for use in detecting micro-organisms in a sample of a substance, comprising a container body having an opening therein, a closure closing said opening, and at least two electrodes, which are contactable with said sample in the container, wherein a chamber is formed internally within the closure and at least a portion of at least one of the electrodes is housed in said chamber, the closure further comprising frangible wall means for separating the chamber from the interior of the container body whereby said portion of said one electrode is isolated from any contents of the container and stored aseptically in the chamber, whereas, when the container is required for use, the wall means can be ruptured to bring the said portion of said one electrode into contact with the contents of the container.

2. A container as claimed in claim 1, wherein the closure comprises an elastomeric bung, and the wall means comprises a membrane integral therewith.

3. A container as claimed in claim 2, further comprising a retaining means for retaining the bung in the opening in the container body.

4. A container as claimed in claim 3, wherein orientation means are provided between the bung and the retaining means for assuring a predetermined orientation of said retaining means relative to said one electrode.

5. A container as claimed in claim 1, wherein the closure comprises a cup-shaped stopper, open inwardly towards the interior of the container body, and the wall means comprises a diaphragm releasably retained adjacent the rim of the cup-shaped stopper.

6. A container as claimed in claim 1, wherein the said at least one of the electrodes is displaceably mounted in the chamber and is adapted to be urged in a direction towards the interior of the container body to rupture the wall means.

7. A container as claimed in claim 6, wherein the container further comprises an annular member threadedly engaged with the container body and cooperable with the said at least one of the electrodes, whereby, on relative rotation between the annular member and container body, the electrode is displaced to cause rupture of the wall means.

8. A container as claimed in claim 1, wherein at least a portion of both of said two electrodes is housed in the chamber or in respective chambers in the closure.

9. A container as claimed in claim 1, wherein the container body comprises a further, resealable opening adapted to enable aseptic introduction of the sample of a substance to the interior of the container.

10. A container as claimed in claim 1, wherein the closure further comprises a portion adapted to enable aseptic introduction of the sample to the interior of the container.

11. A container as claimed in claim 1, wherein the interior of the container body is under reduced pressure, and the wall means are capable of withstanding rupture under a pressure difference of 1 atmosphere.

12. Apparatus for use in detecting micro-organisms comprising a container as claimed in claim 1, in combination with a container-mounting member having means for receiving and locating the container, wherein the receiving and locating means comprises means for cooperating with said one electrode housed in the closure, whereby, when the container is received by the container-mounting member, said one electrode is displaced to cause rupture of the wall means.

13. Apparatus as claimed in claim 12, wherein the container further comprises connecting means co-operable with said receiving and locating means for releasable connection between the container and the container-mounting member.

14. Apparatus as claimed in claim 13, wherein orientation means are provided between the connecting means and the receiving and locating means, and between the connecting means and said one electrode, whereby, when said container is connected to the container-mounting member, the electrode is at a predetermined orientation relative thereto.

* * * * *